United States Patent [19]
Parr et al.

[11] Patent Number: 4,464,469
[45] Date of Patent: Aug. 7, 1984

[54] STABILIZED LACTASE SOLUTIONS AND PROCESSES FOR STABILIZATION

[75] Inventors: Stephen R. Parr, Selby; Geoffrey M. Frost, Brayton, Selby, both of England

[73] Assignee: John & E. Sturge Limited, Selby, England

[21] Appl. No.: 413,461

[22] Filed: Aug. 31, 1982

[30] Foreign Application Priority Data

Sep. 1, 1981 [GB] United Kingdom ............... 8126457

[51] Int. Cl.$^3$ .......................... C12N 9/96; C12N 9/38
[52] U.S. Cl. .................................... 435/188; 435/207
[58] Field of Search ............................. 435/207, 188

[56] References Cited

U.S. PATENT DOCUMENTS

| 3,095,358 | 6/1963 | Meister | 435/188 X |
| 3,242,056 | 3/1966 | Dubois-Prevost | 435/188 |
| 3,413,198 | 11/1968 | Deutsch | 435/188 X |
| 3,515,462 | 6/1970 | Mima et al. | 435/188 |
| 4,329,429 | 5/1982 | Fenton | 435/207 |

FOREIGN PATENT DOCUMENTS 1076750  7/1967  United Kingdom .

OTHER PUBLICATIONS

Yasumatsu et al., Agricultural and Biological Chemistry, vol. 29, No. 7, pp. 665–671 (1965).

*Primary Examiner*—Lionel M. Shapiro
*Attorney, Agent, or Firm*—Hammond & Littell, Weissenberger & Dippert

[57] ABSTRACT

The invention is concerned with the use of sorbitol to stabilize aqueous solutions of yeast lactases. The sorbitol is conveniently used in high concentration so as to act not only as a stabilizing agent but also as an antimicrobial agent. If desired, an antimicrobial agent other than sorbitol can be incorporated. Both aqueous solutions of yeast lactases containing sorbitol and processes for stabilizing aqueous solutions of yeast lactases by incorporation of sorbitol are claimed.

7 Claims, No Drawings

STABILIZED LACTASE SOLUTIONS AND PROCESSES FOR STABILIZATION

This invention relates to stabilised lactase solutions and in particular to lactase solutions having a good storage life at ambient temperature.

Lactases are enzymes used for the hydrolysis of lactose to form glucose and galactose. Such enzymes are for example of use pharmaceutically in the treatment of lactose intolerance, and for this purpose can either be administered directly to the patient or be used in the manufacture of lactose-free dietetic foods. Lactases are also used in the food industry for the sweetening of milk products, such as e.g. cheese whey and for the prevention of lactose crystallisation in milk-containing products such as e.g. ice-cream.

Lactases are generally derived either from yeasts or moulds. Although mould lactases are more stable, it is in general preferred to use lactases derived from yeasts which lactases may be obtained in high yields. It is usual to produce such lactases in the form of aqueous solutions as this facilitates the standardisation of activity of the enzyme product and also provides a convenient form in which to incorporate the enzyme into food products.

Yeast lactases in the form of aqueous solutions are relatively unstable and considerable efforts have been made to find ways of stabilising such yeast lactase compositions. Thus it is known that the stability of the lactase may be increased by buffering the solution to a pH of from 6 to 7. Such buffered solutions have, however, a relatively poor storage life. It has also been found that the lactase stability may be increased by the addition of polyols such as lactose, glycerol and sucrose and such polyols have the advantage that, at high concentrations, they may serve not only as stabilising agents but also as antimicrobial agents. However using the polyols previously described it has still proved necessary to store aqueous solutions of yeast lactases at low temperature if a reasonably long storage life is required.

It has now surprisingly been found that, by using the particular polyol sorbitol as the stabilising agent, aqueous solutions of yeast lactases having a reasonably long storage life at ambient temperatures may be obtained.

Thus, according to the present invention, there is provided an aqueous solution of a yeast lactase containing, as stabilising agent, an effective amount of sorbitol.

A particular advantage of the present invention is that it provides a lactase solution which may be stored for a period of months at ambient temperature without significant loss of enzyme activity. Thus the need for storage at low temperature in order to obtain a long storage life is avoided. A further advantage of aqueous lactase solutions according to the present invention as compared with known aqueous lactase solutions stabilised by reducing sugars such as lactose is that the latter have a tendency to darken and develop bad flavours during storage, as a result of the Maillard reaction between sugar aldehyde groups and amino groups of the enzyme protein, whilst no such tendency has been observed with aqueous lactase solutions stabilised in accordance with the present invention during storage for a period of one year at 25° C.

The aqueous solutions according to the invention conveniently have a lactase concentration of 1,000 to 25,000 EU/milliliter, lactase concentrations of from 1,000 to 12,000 EU/milliliter being preferred in aqueous solutions for use in the dairy industry. One EU is the quantity of lactase which hydrolyses one micromole of lactose in one minute at 30° C. in a 5% w/v solution of lactose buffered at pH 6.2 with potassium phosphate and containing a 10 millimolar concentration of magnesium ions.

The concentration of sorbitol used to obtain the stabilising effect is conveniently from 10 to 80%, preferably from 50 to 70%, by weight of the aqueous solution. The sorbitol is advantageously used in high concentration so as to act not only as a stabilising agent but also as an antimicrobial agent; a preferred concentration of sorbitol for this purpose is not less than about 60% by weight of the aqueous solution. When lower concentrations of sorbitol are used, it may be necessary to add an additional preservative such as e.g. an antimicrobial agent.

When using high concentrations of sorbitol it is generally desirable to use a non-crystallising grade of sorbitol i.e. a slightly impure form in order to reduce any tendency for the sorbitol to crystallise out from the solution. For this reason, it is generally preferred to use about the minimum amount of sorbitol required to obtain the desired stabilising and antimicrobial effect. When incorporating sorbitol in the aqueous solution, it is convenient first to prepare a solution of the enzyme having a sorbitol concentration less than that finally required and then to concentrate the solution to provide the desired final concentration or sorbitol by means of evaporation.

The yeast lactase present in the solutions according to the invention may for example by any of those which are presently available. Such yeast lactases include, for example, lactases produced by culturing strains of *Saccharomyces fragilis* and *Saccharomyces lactis*. One such lactase is that marketed by John & E. Sturge Limited of Selby, Yorkshire, England under the trade mark 'HYDROLACT L50', which lactase is produced by culturing the organism *Saccharomyces fragilis*.

In addition to sorbitol, the lactase solutions according to the invention, may also contain other conventional additives such as for example additional preservatives as mentioned above, enzyme activators e.g. manganese, impurity binders e.g. EDTA and/or buffering agents.

As mentioned above sorbitol exhibits a remarkably improved stabilisation effect at ambient temperature as compared with other known polyol stabilising agents. This effect is illustrated in the following Example:

EXAMPLE 100 g of lactase prepared as hereinafter described were suspended in 500 ml 0.1M potassium phosphate buffer pH 7.0 containing $2 \times 10^{-4}$M $Mn^{2+}$ and $1 \times 10^{-5}$M ethylene diamine tetra-acetate. The suspension was clarified by centrifuging, and the test stabilising agents were added to samples of the supernatant, the pH value of each suspension being adjusted back to 7.0. Samples were stored at 0°–4° C. in the refrigerator and in an incubator at 25° C. for 290 days. Assays for lactase activity were conducted at intervals and rate constants for activity losses were calculated by linear regression. The results, expressed as half-life for lactase activity, are given in Table 1.

TABLE 1

| Stabilising | Half-life for lactase activity (days) | |
|---|---|---|
| agent | 0–4° C. | 25° C. |
| 70% sucrose | 2100 | 147 |
| 70% sorbitol | 2470 | 11,100 |

TABLE 1-continued

| Stabilising agent | Half-life for lactase activity (days) | |
|---|---|---|
| | 0-4° C. | 25° C. |
| 70% lactose | 6670 | 118 |
| 45% glycerol | 958 | 479 |

As will be seen, although at low temperatures (0°-4° C.) the half life obtained with the various polyol stabilising agents was of a similar order of magnitude, at ambient temperature (25° C.) the half life obtained with sorbitol was very considerably higher than those obtained with the other tested polyols.

The lactase used in the above Example was prepared in accordance with the following process:

25 g of Hydrolact S250, a lactase commercially available from John & E. Sturge Limited, was suspended in 500 ml of 0.1M aqueous potassium phosphate buffer (pH 7.0) containing $2 \times 10^{-4}$M $MnCl_2$ and $1 \times 10^{-5}$M ethylene-diaminetetraacetic acid. The suspension was clarified by centrifuging. The supernatant was treated with an equal volume of isopropyl alcohol azeotrope. The precipitate containing the lactase was collected by centrifuging and dried in a vacuum oven at room temperature.

We claim:

1. An aqueous solution of a yeast lactase containing, as stabilizing agent, a stabilizing effective amount of sorbitol.

2. An aqueous solution as claimed in claim 1 which contains at least 10% by weight of sorbitol.

3. An aqueous solution as claimed in claim 1 or claim 2 which contains from 10 to 80% by weight of sorbitol.

4. An aqueous solution as claimed in claim 3 which contains from 50 to 70% by weight of sorbitol.

5. An aqueous composition as claimed in claim 1 which contains an amount of sorbitol which is effective as an antimicrobial agent.

6. An aqueous composition as claimed in claim 1 which contains an antimicrobial agent other than sorbitol.

7. A process for stabilizing an aqueous solution of a yeast lactase which comprises incorporating therein, as stabilizing agent, a stabilizing effective amount of sorbitol.

* * * * *